United States Patent [19]
Humes

[11] Patent Number: 5,911,704
[45] Date of Patent: Jun. 15, 1999

[54] IMPLANTABLE DEVICE AND USES THEREFOR

[75] Inventor: H. David Humes, Ann Arbor, Mich.

[73] Assignee: Nephros Therapeutics, Inc., Ann Arbor, Mich.

[21] Appl. No.: 08/915,033

[22] Filed: Aug. 20, 1997

Related U.S. Application Data

[63] Continuation of application No. 08/461,042, Jun. 5, 1995, Pat. No. 5,704,910.

[51] Int. Cl.[6] .................................................. A61M 11/00
[52] U.S. Cl. .......................................... 604/93; 604/891.1
[58] Field of Search ............................. 604/890.1, 891.1, 604/93, 264, 52, 198, 200

[56] References Cited

U.S. PATENT DOCUMENTS

| | | | |
|---|---|---|---|
| 3,313,289 | 4/1967 | Kapral ......................................... | 128/1 |
| 3,952,747 | 4/1976 | Kimmell, Jr. ........................ | 128/303 R |
| 4,309,776 | 1/1982 | Berguer ............................................ | 3/1 |
| 4,378,016 | 3/1983 | Loeb ........................................ | 128/260 |
| 4,393,133 | 7/1983 | Knowles et al. .............................. | 435/6 |
| 4,479,796 | 10/1984 | Kallok ........................................ | 604/93 |
| 4,494,531 | 1/1985 | Gianturco ................................. | 128/1 R |
| 4,586,922 | 5/1986 | Theeuwes ................................... | 604/85 |
| 4,771,773 | 9/1988 | Kropf ................................... | 128/303 R |
| 4,781,177 | 11/1988 | Lebigot .................................... | 128/897 |
| 4,793,348 | 12/1988 | Palmaz ..................................... | 128/325 |
| 4,793,825 | 12/1988 | Benjamin et al. .................... | 604/891.1 |
| 4,817,600 | 4/1989 | Herms et al. ........................ | 128/303 R |
| 4,994,069 | 2/1991 | Ritchart et al. ........................... | 606/191 |
| 5,026,365 | 6/1991 | Rossini et al. ....................... | 604/891.1 |
| 5,053,008 | 10/1991 | Bajaj ...................................... | 604/104 |

(List continued on next page.)

FOREIGN PATENT DOCUMENTS

| | | |
|---|---|---|
| 0 341 039 A1 | 11/1989 | European Pat. Off. . |
| 0 598 635 A1 | 11/1992 | European Pat. Off. . |
| 0 604 022 A1 | 6/1994 | European Pat. Off. . |
| 34 47 202 C2 | 4/1986 | Germany . |
| 39 41 873 A1 | 6/1991 | Germany . |
| WO 89/04655 | 6/1989 | WIPO . |
| WO 90/06997 | 6/1990 | WIPO . |
| WO 92/15676 | 9/1992 | WIPO . |
| WO 93/06878 | 4/1993 | WIPO . |
| WO 94/15583 | 7/1994 | WIPO . |
| WO 95/00654 | 1/1995 | WIPO . |

OTHER PUBLICATIONS

Aebischer et al. (1991) "Transplantation of Microencapsulated Bovine Chromaffin Cells Reduces Lesion–induced Rotational Asymmetry in Rats," *Brain Research* 560: 43–49.

Albert et al. (1992) "Evaluation of Various Gene Transfection Methods Into Human Myoblast Clones," *Transplantation Proceedings* 24 : 2784–2786.

Crystal, R.G. (1992) "Gene Therapy Strategies for Pulmonary Disease," *The American Journal of Medicine* 92: 6A–44S–6A–52S.

Dwarki et al. (1995) "Gene Therapy for Hemophilia A: Production of Therapeutic Levels of Human Factor VIII in vivo Mice," *Proc. Natl. Acad. Sci. USA* 92 : 1023–1027.

Garver et al. (1987) "Clonal Gene Therapy: Transplanted Mouse Fibroblast Clones Express Human α1–Antitrypsin Gene in Vivo," *Science* 237: 762–764.

(List continued on next page.)

*Primary Examiner*—Wynn Wood Coggins
*Assistant Examiner*—Deborah Blyveis
*Attorney, Agent, or Firm*—Testa, Hurwitz & Thibeault, LLP

[57] ABSTRACT

Disclosed is an implantable device for delivering a preselected molecule, for example, a hormone, into a mammal's systemic circulation. The device comprises a blood permeable element that can be anchored to an inner wall of an intact blood vessel. The device also comprises a capsule that is held in place within the blood vessel by the anchored blood permeable element. The capsule encloses viable cells which produce and secrete the preselected molecule into blood passing the capsule. The invention also provides a minimally invasive method for percutaneously introducing into a preselected blood vessel the device of the invention.

47 Claims, 3 Drawing Sheets

U.S. PATENT DOCUMENTS

| | | | |
|---|---|---|---|
| 5,059,205 | 10/1991 | El-Nounou et al. | 606/200 |
| 5,104,399 | 4/1992 | Lazarus | 623/1 |
| 5,147,379 | 9/1992 | Sabbaghian et al. | 606/206 |
| 5,152,777 | 10/1992 | Goldberg et al. | 606/200 |
| 5,164,186 | 11/1992 | Tsuru et al. | 424/422 |
| 5,182,111 | 1/1993 | Aebischer et al. | 424/424 |
| 5,304,120 | 4/1994 | Crandell et al. | 604/52 |
| 5,314,471 | 5/1994 | Brauker et al. | 623/11 |
| 5,350,398 | 9/1994 | Pavcnik et al. | 606/200 |
| 5,383,887 | 1/1995 | Nadal | 606/200 |
| 5,383,892 | 1/1995 | Cardon et al. | 606/198 |
| 5,443,508 | 8/1995 | Giampapa | 623/11 |
| 5,487,739 | 1/1996 | Aebischer et al. | 604/890.1 |

OTHER PUBLICATIONS

Glaser, V. (1995) "Bioreactor and Fermenter Suppliers" *Genetic Engineering News Feb. 1, 1995.*

Goldberg et al. (1987) "The regulated Expression of Erythropoietin by Two Human Hepatoma Cell Lines," *Proc. Natl. Acad. Sci. USA 84*: 7972–7976.

Greenfield et al. (1973) "A New Intracaval Filter Permitting Continued Flow and Resolution of Emboli," *Surgery 73*: 599–606.

Greenfield et al. (1977) "Clinical Experience with the Kim–Ray Greenfield Vena Caval Filter," *Ann. Surg. 185*: 692–698.

Greenfield et al. (1981) "Greenfield Vena Caval Filter Experience," *Arch Surg* 116: 1451–1456.

Greenfield et al. (1989) "Venous Interruption," Chapter 68 in *"Haimovici's Vascular Surgery Principles and Techniques, 3rd Ed"* pp. 929–940.

Greenfield L.J. (1991) "Venous Thromboembolic Disease," Chapter 37 in *"Vascular Surgery, A Comprehensive Review,"* Moore, Ed., pp. 669–679.

"Instructions for Use Titanium Greenfield Vena Cava Filter with 12 French Introducer System" 1–48, by *Meditech, Boston Scientific Corporation.*

Hamamori et al. (1995) "Myoblast Transfer of Human Erythropoietin Gene in Mouse Model of Renal Failure," *J. Clin. Invest.* 95: 1808–1813.

Hoeben et al. "Toward Gene Therapy in Haemophilia A: Retrovirus–Mediated Transfer of a Factor VII Gene into Murine Haematopoietic Progenitor Cells," 341–345.

Jelkmann, W. (1992) "Erythropoietin: Structure, Control of Production, and Function," *Physiological Reviews* 72: 449–489.

Lacy et al. (1976) "Long–term Perifusion of Isolated Rat Islets in Vitro," *Diabetes* 25: 484–493.

Lozier et al. (1994) "Gene Therapy and the Hemophilias," *JAMA* 271: 47–51.

Maxwell et al. (1993) "Identification of the Renal Erythropoietin–producing Cells Using Transgenic Mice," *Kidney International* 44: 1149–1162.

Nashitz et al. (1993) "Thromboembolism in Cancer," *Cancer* 71: 1384–1390.

Radovich, J.M. (1995) "Composition of Polymer Membranes for Therapies of End–Stage Renal Disease," *Bonomini V, Berland Y (eds): Dialysis Membranes: Structure and Predictions. Contrib Nephrol. Basel, Karger* 113: 11–24.

Roman et al. (1992) "Circulating Human or Canine Factor IX from Retrovirally Transduced Primary Myoblasts and Established Myoblast Cell Lines Grafted into Murine Skeletal Muscle," *Somatic Cell and Molecular Genetics* 18: 247–258.

Tripathy et al. (1994) "Stable Delivery of Physiologic Levels of Recombinant Erythropoietin to the Systemic Circulation by Intramuscular Injection of Replication–defective Adenovirus," *Proc. Natl. Acad. Sci. USA* 91: 11557–11561.

Wollheim et al. (1990) "Isolation of Pancreatic Islets and Primary Culture of the Intact Microorgans or of Dispersed Islet Cells," *Methods in Enzymology* 192: 188–223.

Wollheim et al. (1990) "Establishment and Culture of Insulin–Secreting $\beta$ Cell Lines" *Methods in Enzymology* 192: 223–225.

Kurachi et al. (1993) "Gene Therapy of Hemophilia B" Thromb. Haemost., 70: 193–197.

Yao et al. (1992) "Expression of Human Factor IX in Mice After Rejection of Genetically Modified Myoblasts," Proc. Natl. Acad. Sci., 89 :3357–3361.

Yao et al. (1993) "Implanted Myoblasts Not Only Fuse With Myofibers But Also Survive as Muscle Precursor Cells," Journal of Cell Science, 105:957–063.

Yao et al. (1994) "Primary Myoblast–mediated Gene Transfer: Persistent Expression of Human Factor IX In Mice," Gene Therapy, 1:99–107.

Copy of International Search Report for counterpart International application PCT/US96/08524.

IMPLANTABLE DEVICE AND USES THEREFOR

This application is a continuation of U.S. Ser. No. 08/461,042, filed Jun. 5, 1995, now U.S. Pat. No. 5,704,910.

FIELD OF THE INVENTION

The present invention relates to an implantable device for delivering a pre-selected molecule into systemic circulation. More particularly, this invention relates to an implantable device containing viable cells. When the device is implanted into a blood vessel, the cells produce and secrete the pre-selected molecule into blood circulating past the device.

BACKGROUND OF THE INVENTION

The development of drug delivery devices for implantation into a pre-selected locus in a mammal is ongoing. To date, a variety of surgically implantable drug delivery devices have been developed and are discussed below.

U.S. Pat. No. 4,378,016 describes a surgically implantable device for delivering an active factor, for example, a hormone, to a pre-selected site, for example, the peritoneal cavity, of a mammal. The device comprises a fluid permeable membranous sack for implantation within the mammal and an impermeable hollow tube having one end connected to an opening in the sack and the other end designed to remain outside the body of the mammal. The tube provides an access passageway to the membranous sack, such that after the sack has been surgically implanted into the mammal, a cell containing envelope may be introduced into the sack via the tube. Upon insertion of the cell containing envelope into the sack, the cells may produce an active factor, which subsequently may diffuse into the surrounding tissue or organ of the recipient.

U.S. Pat. No. 5,182,111 describes a surgically implantable device for delivering an active factor to a pre-selected site, for example, a tissue or organ, in a mammal. The device comprises a semi-permeable membrane enclosing at least one cell type that produces a specific active-factor and a second cell type that produces an augmentory factor. The augmenting factor produced by the second cell type subsequently induces the first cell type to produce the active-factor.

U.S. Pat. No. 4,479,796 describes a surgically implantable dispenser for infusing a pre-selected drug directly into the blood stream. Briefly, the dispenser is surgically spliced in line with a blood vessel. The dispenser encloses a replaceable cartridge of cells, for example, micro-organisms, which produce and secrete the drug into blood flowing past the cartridge.

U.S. Pat. No. 4,309,776 describes an intravascular drug delivery device having a chamber containing transplanted cells for surgical implantation into the wall of a blood vessel. The device comprises a porous wall that permits a hormone produced by the transplanted cells to diffuse out of the chamber and into the blood stream.

It is desirable, however, to produce a device that may be implanted into a mammal by either non-surgical or only minimally invasive surgical procedures, and that once implanted the device secretes a pre-selected molecule directly into the vasculature. In addition, it is desirable to produce a device which, when implanted, administers the pre-selected molecule into the mammal over an extended period and may be removed conveniently, if or whenever the necessity arises. Accordingly, it is an object of the present invention to provide an easily implantable device for delivering, over long periods of time, a pre-selected molecule into the systemic circulation of a mammal. It is another object to provide a method for non-surgically implanting the device into a blood vessel of a mammal for delivering the pre-selected molecule into systemic circulation.

These and other objects and features of the invention will be more clearly understood from the description, drawings, and claims which follow.

SUMMARY OF THE INVENTION

The present invention provides an implantable device for delivery of a pre-selected molecule into the systemic circulation of a mammal. The device of the invention may be implanted using non- or minimally invasive surgical procedures and, once implanted, delivers the pre-selected molecule directly into the blood stream. In addition, the device of the invention is adapted to produce in situ and thereafter secrete the pre-selected molecule into the blood stream over a prolonged period of time. Use of the present device and method provides an easy and reproducible system for delivering therapeutically effective amounts of a gene product, for example, a hormone, growth factor, anti-coagulant, immunomodulator, cytokine, or the like, directly into the blood stream of the recipient. The devices of the present invention, although having a variety of utilities, are particularly suited for use in hormone replacement therapy.

In its broadest aspect, the device comprises a blood permeable element, which is adapted for anchorage to an inner surface of a blood vessel. The blood permeable element, as disclosed herein, is designed such that when anchored to the inner surface of the blood vessel, the element permits blood in the vessel to pass therethrough. The device further comprises a capsule that may be positioned, and retained in place, by contacting. the element disposed within the vessel. The capsule contains viable cells which produce and secrete the pre-selected molecule into the blood stream.

The term "systemic circulation" as used herein is understood to embrace any blood vessel within a mammal, i.e., an artery, arteriole, venule or vein, that provides a blood supply to all tissues, except lung tissues perfused by the pulmonary circulation, of a mammal. The systemic circulation is also referred to in the art as the greater circulation or the peripheral circulation.

The term "blood permeable element" as used herein is understood to mean any structure for insertion into the lumen of a blood vessel in the systemic circulation that, once inserted, may be anchored, for example, by hooks or barbs, to an inner surface of the blood vessel. The element being further characterized in that when anchored to the inner wall of the blood vessel, the element does not occlude or prevent blood flow through the blood vessel.

In a preferred embodiment, the blood permeable element is an embolism anti-migration filter, such as a blood clot anti-migration filter. A variety of blood clot anti-migration filters useful in the practice of the invention are known in the art. The currently preferred blood permeable element is an anti-migration filter known as a "Greenfield® vena cava filter". Useful Greenfield® vena cava filters are described in detail in U.S. Pat. Nos. 4,817,600 and 5,059,205, the disclosures of which are incorporated by reference herein.

The term "capsule" as used herein is understood to mean any hollow structure dimensioned to fit within the lumen of a blood vessel, which, when introduced into the blood vessel, does not occlude or prevent blood flow through the vessel. The capsule is held in place within the blood vessel by means of the blood permeable element. For example, the capsule may be retained upstream of the blood permeable element when the capsule is of a size such that it cannot pass through the blood permeable element. Alternatively, the blood permeable may be located downstream of the blood permeable element but retained in place by an attachment means, for example, a hook or tether, extending from the blood permeable element to the capsule. In addition, it is contemplated that the capsule may be wedge-like in shape, such that the narrow end of the wedge may pass through the element but the larger end contacts the element thereby to prevent passage of the capsule through the element.

The capsule may comprise either a single hollow fiber or a bundle of hollow fibers made from a semi-permeable membrane. The semi-permeable membrane preferably has pores of a size sufficient to permit the diffusion of the pre-selected molecule therethrough but yet small enough to exclude the passage of cells therethrough. The pores preferably are designed to permit the pre-selected molecule produced by the cells to diffuse directly into the blood stream passing the hollow fiber while preventing the cells from migrating out of the hollow fiber and into the systemic circulation. More specifically, the pores preferably are dimensioned to allow solutes having a molecular weight of less than about 150 kilo daltons to pass therethrough while excluding agents in the blood stream, for example, proteins, specifically, antibodies and cytolytic factors secreted by lymphocytes, or cells, specifically, macrophages and lymphocytes, which if allowed to pass though the pores from the blood stream into the hollow fiber may be detrimental to the viability of the cells enclosed therein. It is contemplated that if the preselected molecule has a molecular weight greater than about 150 kilo daltons then the capsule should have pores dimensioned to permit the preselected molecule to diffuse out of the capsule into the blood stream. It should be noted, however, that the viable cells useful in producing and secreting preselected molecules having a molecular weight greater than 150 kilo daltons should be autologous in nature thereby minimizing a host immune response, humoral and/or cellular, directed against the cells disposed within the capsule.

Polymers useful in producing biocompatible semi-permeable membranes of the present invention include, but are not limited to, polyvinylchloride, polyvinylidene fluoride, polyurethane isocyanate, polyalginate, cellulose acetate, cellulose diacetate, cellulose triacetate, cellulose nitrate, polysulfone, polystyrene, polyurethane, polyvinyl alcohol, polyacrylonitrile, polyamide, polymethylmethacrylate, polyethylene oxide and polytetafluoroethylene. In addition, it is contemplated that useful semi-permeable membranes may be produced from a combination of such polymers.

In another preferred embodiment, the viable cells enclosed within the semi-permeable hollow fiber(s) of the capsule, preferably are eukaryotic cells, and most preferably are mammalian cells. Although, the device described herein may comprise cells which naturally produce and secrete the pre-selected molecule, it is contemplated that genetically engineered cells, i.e., cells transfected with, and capable of expressing a nucleic acid encoding the pre-selected molecule, may likewise be used in the practice of the invention.

In another preferred embodiment, the pre-selected molecule preferably is a protein, and most preferably is a hormone, for example, erythropoietin or insulin. It is contemplated, however, that the device may be used to deliver into the systemic circulation any molecule that can be produced and secreted from a viable cell. Although single cell types that produce and secrete a single pre-selected molecule may be used in the invention, it is understood that cells belonging to a particular cell type that produce and secrete a plurality of pre-selected molecules likewise may be used in the practice of the instant invention. Similarly, it is contemplated that a plurality of cell types, wherein cells belonging to each cell type produce and secrete different pre-selected molecules, may be combined in a capsule thereby to produce a device that delivers a desirable combination of preselected molecules into the circulation.

In some applications, for example, during hormone replacement therapy, it is preferable to use cells which produce the pre-selected molecule in response to an external stimulus. A device containing such regulated cells therefore produces the pre-selected molecule when the necessity arises thereby preventing an overproduction of the pre-selected molecule, which, depending upon the molecule, may be detrimental to the recipient. However, during other applications, for example, during replacement therapy of Factor VIII in Factor VIII deficient hemophilia; Factor IX in Factor IX deficient hemophilia; or $\alpha_1$-anti-trypsin in $\alpha_1$-anti-trypsin deficient emphysema, it is contemplated that cells which constitutively produce these pre-selected molecules, may be enclosed in the hollow fibers of the device.

Certain forms of anemias, for example, erythropoietin deficient anemias caused by end stage renal disease, result from the inability of the host to produce erythropoietin in an amount sufficient to induce the production of sufficient numbers of red blood cells. As a result of this disease, the patient's red blood cell mass falls thereby lowering the oxygen carrying potential of the blood. In one preferred embodiment, the invention therefore provides a device comprising erythropoietin producing cells that produce erythropoietin in response to the reduced oxygen carrying capacity of the recipient's blood. The invention permits the erythropoietin producing cells to be exposed to blood intimately enough so that full endocrine function of the cells can be realized effectively. Accordingly, it is contemplated that the implantable erythropoietin producing and secreting device of the invention may be useful in the treatment of erythropoietin deficient anemias.

In addition, certain forms of diabetes, for example, diabetes mellitus, result from an inability of the host to produce insulin in an amount sufficient to modulate the level of circulating glucose in the blood stream. In another preferred embodiment, the invention provides a device comprising insulin producing cells that produce insulin in response to the level of glucose in the blood. Accordingly, it is contemplated that the implantable insulin producing and secreting device of the invention may be useful in the treatment of insulin dependant forms of diabetes.

In another aspect, the invention provides a method for percutaneously introducing into a blood vessel of a mammal, a device for delivering a pre-selected molecule into systemic circulation. The method comprises the steps of: (a) anchoring a blood permeable element to an inner wall of an intact blood vessel, which when anchored permits blood in the vessel to pass therethrough; (b) introducing at a location upstream of the anchored element a capsule containing viable cells that produce and secrete the pre-selected molecule; and (c) permitting the capsule to contact the element.

In this procedure, the blood permeable element may be introduced into the blood vessel by means of a catheter.

Furthermore, the capsule may likewise be introduced into the vessel by means of the same or a different catheter. During such procedures the blood permeable element and/or the capsule may be introduced by a catheter into the mammal via a femoral or jugular vein and then anchored in a natural vein, for example, an inferior vena cava, a superior vena cava, a portal vein or a renal vein, or alternatively, anchored in a synthetic vein, for example, a vein developed from a surgically-developed arteriovenous fistula. It is contemplated that selection of appropriate sites for introduction and anchorage of the device is within the expertise of one skilled in the art.

BRIEF DESCRIPTION OF THE DRAWINGS

The present invention will now be more particularly described with reference to and as illustrated in, but in no manner limited to, the accompanying drawings, in which.

In the drawings, like characters in the respective drawings indicate corresponding parts.

DETAILED DESCRIPTION OF THE INVENTION

In its most general application, the present invention provides an implantable device for delivering a pre-selected molecule into the systemic circulation of a mammal. The device of the invention is adapted for direct implantation into a blood vessel, preferably using a catheter. After implantation, the device permits the pre-selected molecule to diffuse out of the device and into the blood stream of the recipient, which in certain aspects does so in response to blood parameters, for example, oxygen tension in the case of erythropoietin-producing cells.

The device comprises two components that interact with one another when implanted in the recipient. The first component is a blood permeable element, preferably a cage-like filamentous structure, that is dimensioned for insertion into the lumen of an intact blood vessel. Once introduced to a desired location, the element is anchored in place to an inner wall of the blood vessel typically by means of hooks or barbs disposed upon the element. The blood permeable element is designed such that when anchored to the wall of the blood vessel, the element permits blood in the vessel to pass therethrough. The second component is a capsule also dimensioned for insertion into the lumen of the blood vessel. The capsule comprises a semipermeable housing containing viable cells which produce and secrete the pre-selected molecule. The capsule is inserted into the blood vessel upstream of the element. Once inserted, the capsule may move along the blood vessel with the flow of the blood until it reaches and contacts the anchored element. The pre-selected molecule is produced and secreted by the cells entrapped within the capsule, which after being secreted from the cells diffuses out of the capsule and into blood passing the capsule. Upon entry into the blood stream, the pre-selected molecule is disseminated rapidly throughout the vasculature of the host. Proper operation of the device requires that it not occlude the blood vessel, i.e., the implanted device does not prevent passage of blood through the blood vessel.

Figure 1:
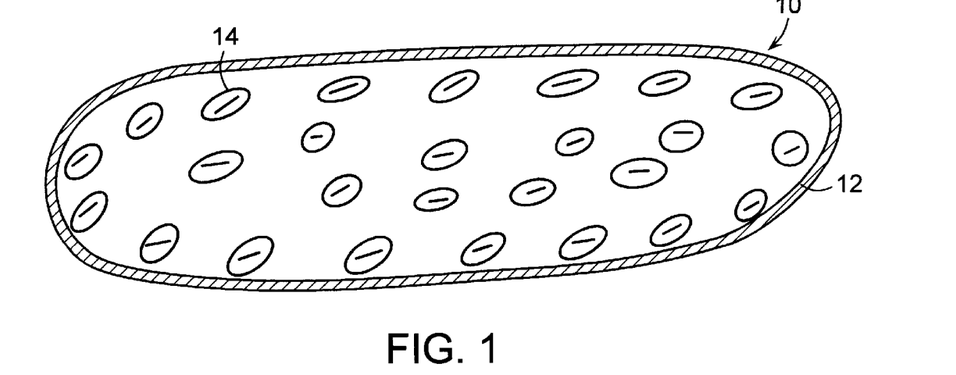
FIG. 1 is a side sectional schematic illustration of a first cell-containing capsule of the type useful in the practice of the present invention.
Figure 2:
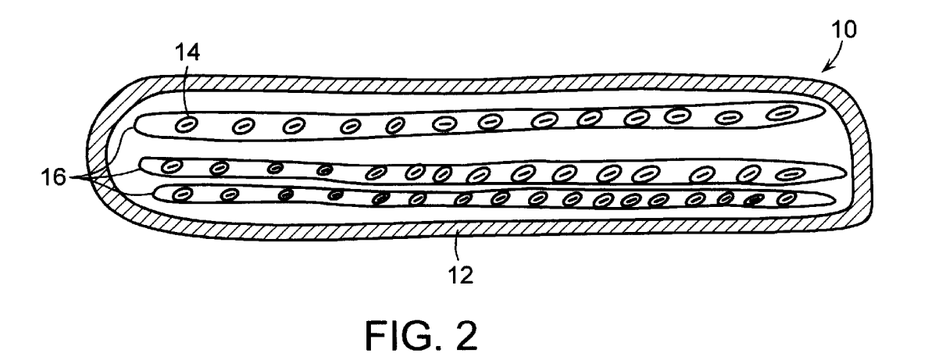
FIG. 2 is a side sectional schematic illustration of a second cell-containing capsule of the type useful in the practice of the present invention.

The device of the present invention will now be described in greater detail with reference to the attached drawings, which are provided for purposes of illustration and are not meant to be limiting of the scope of the invention. Referring to the drawings, FIGS. 1 and 2 illustrate schematically capsules 10 useful in the practice of the invention. In FIG. 1, the capsule 10 comprises a single hollow fiber made of a semi-permeable membrane 12 which encloses the viable cells 14. In FIG. 2, the capsule 10 comprises a semi-permeable membrane 12 enclosing a plurality of semi-permeable membrane hollow fibers 16 which enclose the viable cells 14. It is contemplated that semi-permeable membranes 12 and 16 may be defined by either the same or different polymeric compositions. Methods and materials for the manufacture of such membranes are known in the art, and are described below. The viable cells 14 may, or may not, be attached to an inner surface of a fiber, however, this feature will depend upon the cell type included in the device. For example, some cell types grow in an anchorage dependent manner upon a solid surface while other cell types have no anchorage dependency and grow in suspension. The choice of cell type, however, is dependent upon the resulting application.

Figure 3:
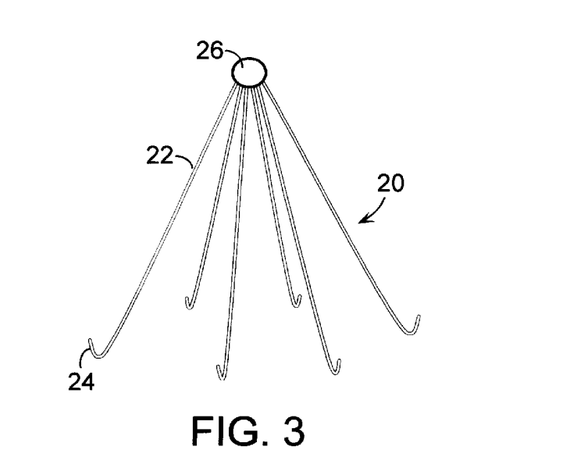
FIG. 3 is an illustration depicting a preferred blood permeable element of the invention.
Figure 4:
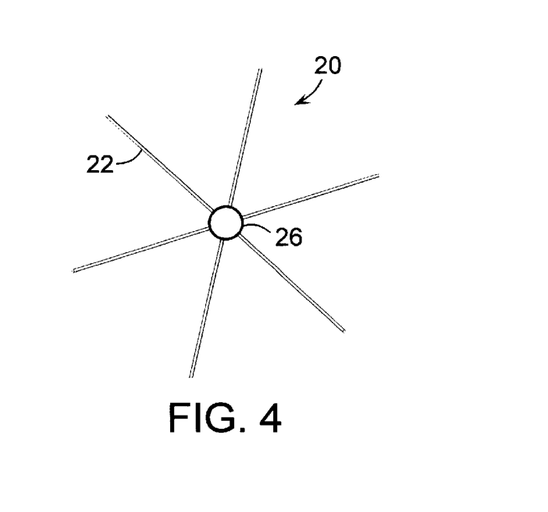
FIG. 4 is a top plan view of the element of FIG. 3.

FIGS. 3 and 4, show a preferred blood permeable element 20 useful in the practice of the invention. The element 20 comprises a head 26 and a plurality of resilient, typically metallic, legs 22 extending therefrom. The end of the legs distal to the head comprise hooks or barbs 24 disposed outwardly to engage an inner wall of the target blood vessel. A variety of such elements based upon this design are well known in the art, and are described in more detail below. It is contemplated, however, that other blood permeable elements based upon other designs, for example, a birds nest filter described hereinbelow, also may be used in the practice of the instant invention.

Figure 5:
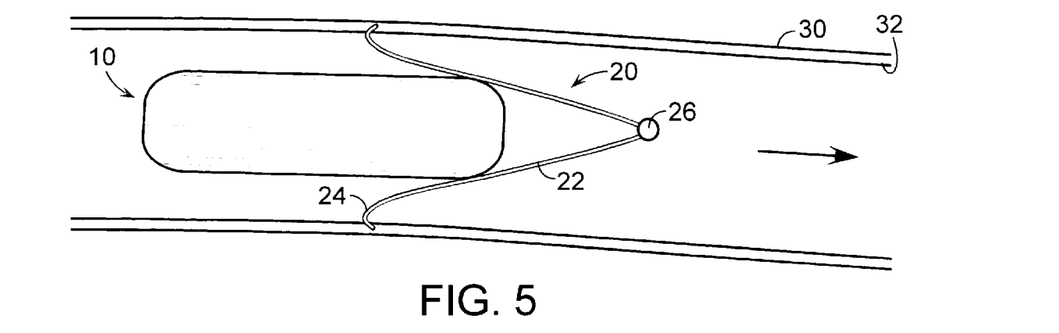
FIG. 5 is a cross-sectional schematic view of the device of the invention disposed within an intact blood vessel.
Figure 6A:
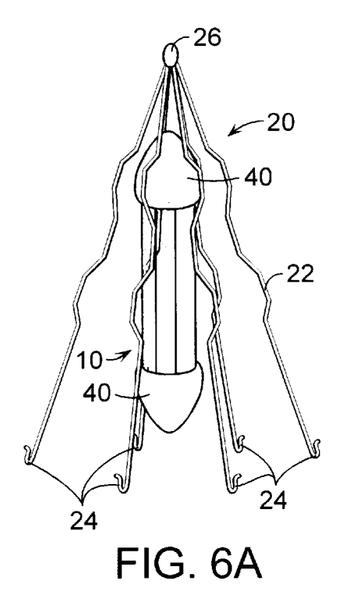
FIGS. 6A through 6E are illustrations showing preferred embodiments of the device of the invention.
Figure 6B:
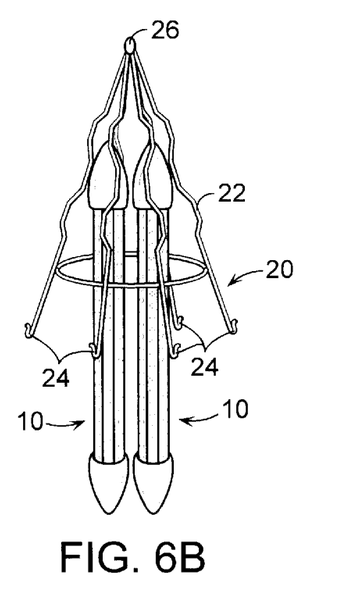
Figure 6C:
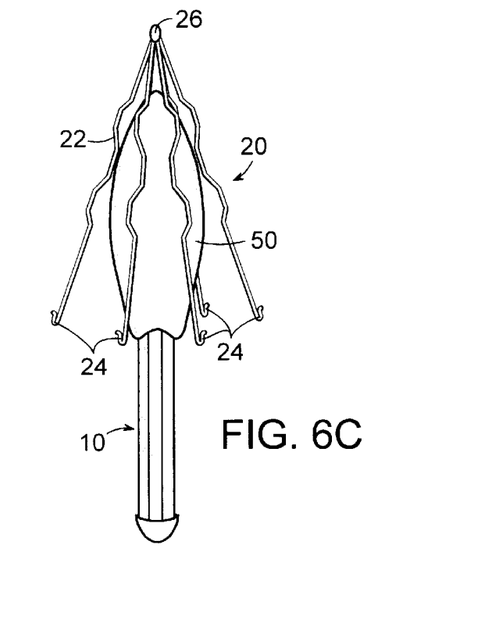
Figure 6D:
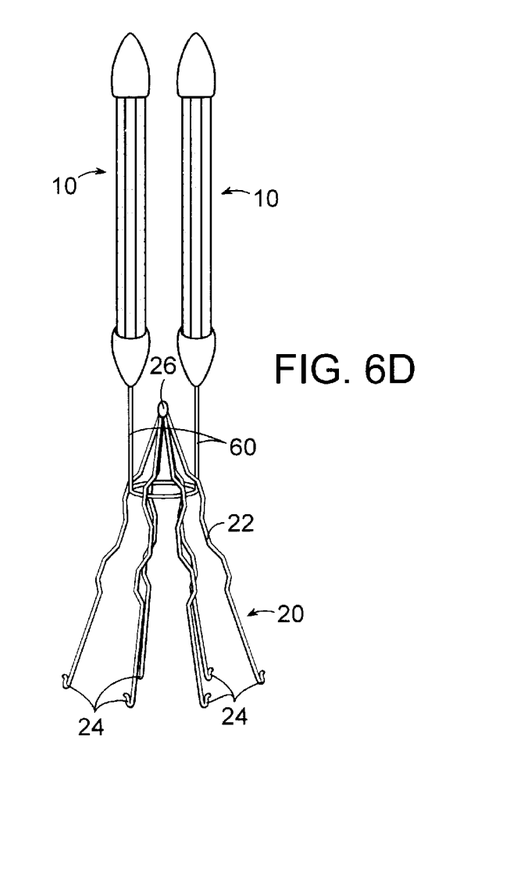
Figure 6E:
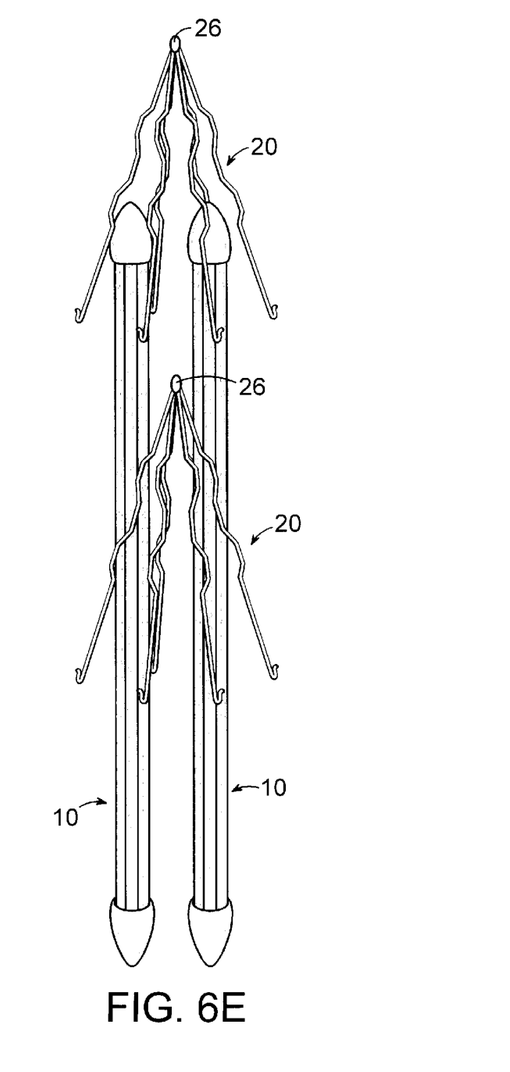

FIG. 5, shows a preferred design configuration for the implantable device of the invention. The blood permeable element 20 is anchored to an inner wall 32 of an intact blood vessel 30. The head 26 of the element 20 having legs 22 extending therefrom biased radially by spring tension is located in the vessel proximal to the hooks 24. The outwardly disposed legs 22 spread, umbrella-like, to permit hooks 24 to engage the wall of the blood vessel 30 to prevent movement of the element in the direction of blood flow (shown by the arrow). Located upstream of the element 20 is a capsule 10 containing viable cells. The capsule is made of a semi-permeable membrane that permits oxygen, glucose and other nutrients necessary for the viability of the encapsulated cells to diffuse from the blood stream into the lumen of the capsule while permitting cell metabolites, for example, the pre-selected molecule and cellular waste products, to diffuse out of lumen of the capsule into the blood stream.

FIG. 6 shows a variety of configurations believed to be useful in the practice of the invention. FIG. 6A shows a single capsule 10 comprising a bundle of hollow fibers held together by means of end caps 40. The single capsule is disposed within a single blood permeable element 20. Assuming that the hooks or barbs 24 are embedded into the inner wall of a blood vessel, then capsule 10 is retained in position within the blood vessel upstream of the blood permeable element by contact with the blood permeable element 20. FIG. 6B is essentially the same as FIG. 6A except that two capsules 10 are disposed within and in contact with a single blood permeable element 20. FIG. 6C shows a single capsule 10 retained within and in contact with a blood permeable element 20. Part of capsule 10 contacting the blood permeable element 20 is disposed within a biocompatible gel 50, for example, an autologous blood clot, thereby to optimize capture of the capsule 10 by the blood permeable element 20. FIG. 6D shows two capsules 10 retained in place by a blood permeable element 20. The capsules 10, contact the blood permeable element 20 by means of hooks or tethers 60. Assuming that barbs 24 of the blood permeable element 20 are embedded into an inner wall of a blood vessel, then the capsules 10 would be located downstream of the blood permeable element. FIG. 6E shows two capsules 10 held in place by means of two blood permeable elements 20. This type of configuration may be particularly useful when a large number of cells may be required to produce the preferred dosage of pre-selected molecule and, therefore, long capsules 10 are required to accommodate the large number of viable cells.

The Blood Permeable Element

As mentioned above, the art is replete with blood permeable elements useful in the practice of the instant invention. Useful blood permeable elements are characterized by their ability to be anchored within the lumen of a blood vessel without occluding or preventing blood flow through the blood vessel.

Blood permeable elements useful in the practice of the invention are commercially available and are marketed as embolism or blood clot anti-migration filters. These anti-migration filters are used routinely by medical practitioners to prevent the migration of potentially life threatening blood clots within the vasculature. Blood clot anti-migration filters typically are designed to be implanted and anchored within the lumen of a blood vessel. When implanted, the anti-migration filters permit blood in the vessel to pass while simultaneously trapping blood clots.

A variety of blood clot anti-migration filters useful in this invention are known in the art and are commercially available. For example, currently preferred blood clot anti-migration filters described in U.S. Pat. Nos. 4,817,600 and 5,059,205, referred to in the art as Greenfield® filters and available from Medi.Tech®, Boston Scientific Corporation, Watertown, Mass., are particularly well suited to the practice of the invention. The cone-shaped Greenfield® vena cava filters are designed to provide maximal entrapment area for trapping blood clots while maintaining patency of the blood vessel after trapping emboli. For example, the geometry of the cone permits filling to 80% of its depth before the cross-sectional area is reduced by 64%, and that at least 80% of the depth of the filter can be filled without development of a significant pressure gradient across the filter. The spacing between the six legs of the Greenfield® vena cava filters ensures the trapping of emboli greater than 3 mm (Greenfield et al. (1989) "Venous Interruption" Chapter 68, pp. 929–939 in "*Haimovici's Vascular Surgery Principles and Techniques, Third Edition*," Appleton and Lange, Norwalk, Conn./San Mateos, Calif.). Accordingly, the filters may be able to capture capsules greater than 3 mm in diameter.

Other useful blood clot anti-migration filters useful in the invention are described in U.S. Pat. Nos. 4,781,177; 4,494,531; 4,793,348; 5,152,777; 5,350,398; and 5,383,887, the disclosures of which are incorporated herein by reference.

Also, it is contemplated that other blood clot anti-migration filters, such as those described in Greenfield (1991) in "*Vascular Surgery, A Comprehensive Review*" Moore, ed. W.B. Saunders Co., Philadelphia, London, Toronto, Montreal, Sydney, Tokyo pp. 669–679, including: Nitinol filters; Gunther filters; Venatech filters; Amplatz filters; and birds nest filters, likewise may be useful in the practice of the invention. Because of the inherent properties of blood clot anti-migration filters, namely their design for introduction and anchorage within the lumen of a blood vessel, and further that, when anchored in the vessel, the filters permit blood in the vessel to pass therethrough, makes them desirable as blood permeable elements of the invention. It is contemplated, however, that blood permeable elements other than the ones described herein but having the aforementioned characteristics also may be useful in the practice of the instant invention.

Capsule Design.

The implanted drug delivery device of the invention may be capable of delivering a pre-selected drug over a prolonged period of time, preferably in range of months to years. It is contemplated, however, that exhausted cell capsules, i.e., wherein a substantial fraction of cells within the capsule are no longer viable or no longer secrete the pre-selected molecule, may be retrieved from the recipient and replaced with new capsules containing fresh cells that produce and secrete the pre-selected molecule.

The capsule may comprise either a single hollow fiber (as shown in FIG. 1) or a plurality of hollow fibers (as shown in FIG. 2). The number of fibers depend upon a set of variables that may be determined without undue experimentation. One variable, for example, includes the productivity of the cells to be incorporated into the device. It is appreciated that if a first cell type produces and secretes more pre-selected molecule than a second cell type, then fewer cells of the first type will be needed to produce the same amount of pre-selected molecule. Other variables include: the amount of the pre-selected molecule necessary to produce the desired therapeutic effect in the recipient; the nutritional requirements of the cells; the time over which the cells remain viable after implantation; and the density to which the cells can grow without losing viability. Once these variables have been established, then the practitioner by judicious choice of cell type and hollow fiber geometry may select the appropriate cell type to remain viable in the host and produce the desired amount of pre-selected molecule for the longest period of time.

Because the device permits delivery of the pre-selected molecule over prolonged periods of time, an important consideration, therefore, is the development of capsules which maintain the viability of the cells enclosed therein after implantation into the host. It is understood that a variety of factors, for example: the supply of oxygen and nutrients to the cells in the capsule; the removal of waste products from the cells in the capsule; the minimization of host immune responses directed against the cells in the capsule; the proliferative activity of the cells; and whether cells located at the center of the capsules are susceptible to pressure necrosis, all of which may influence the design and preparation of a cell containing capsule.

Since the transport of oxygen may become a limiting factor for the viability and function of implanted cells, the geometry of the hollow fibers must be chosen with care to maintain adequate oxygen delivery. It is believed that the transport of oxygen from the lumen of the blood vessel to the cells enclosed within the capsule occurs almost exclusively by diffusion. Studies have shown that, in order to maintain the viability of cells excluded from the blood stream or a blood supply, the cells preferably are located within a critical diffusion distance of about 500 μm, more specifically about 300 μm from the blood supply. For example, direct measurement of the dissolved oxygen levels in mammalian thoracic aortas with oxygen electrodes have shown that the level of dissolved oxygen in the arterial wall approaches a nadir of 25 mm Hg approximately 300 μm from the blood lumen (Buerk et al. (1982) *Am. J. Physiol.* 243: H948–H958). In order to ensure optimal aeration conditions, it is contemplated therefore that the hollow fibers containing the cells should have an internal diameter preferably less than about 1000 μm (1.0 mm), and most preferably less than about 500 μm (0.5 mm). It should be noted that cells that have a low metabolic activity, and therefore low oxygen demand, for example, myoblasts may remain viable in hollow fibers having internal diameters exceeding about 500 μm, however, cell types with high metabolic activities preferably are entrapped within hollow fibers having internal diameters of about 200 μm. Furthermore, it is contemplated that the optimal capsule diameter for a pre-selected cell type may be determined without undue experimentation using the methodolgies described hereinbelow In addition to adequate aeration, it is important that the encapsulated cells obtain sufficient amounts of essential nutrients from the blood supply to remain viable. It is believed that oxygen diffusion is the most important aspect in maintaining cell viability and, therefore, once the geometry of a hollow fiber has been optimized for oxygen transport, then the hollow fiber inherently will be able to permit the diffusion of adequate amounts of nutrients into the lumen of the capsule from the blood stream. Similarly, such a geometry is contemplated also to permit diffusion of cell metabolites, including, waste products and the pre-selected molecule, out of the hollow fiber and into the blood stream.

The hollow fibers preferably are produced from a semi-permeable membrane having pores dimensioned to permit the diffusion of oxygen and nutrients into the lumen of the hollow fiber while permitting the efflux of cellular waste products and the pre-selected molecule out of the hollow fiber. In addition, the pores preferably are dimensioned to exclude the passage of cells therethrough. Accordingly, the pores are designed to prevent migration of the viable cells from the lumen of the hollow fiber into the blood steam, thereby maintaining the implanted cells at a single location in the host to facilitate their subsequent removal if or when necessary. The pores also are designed to prevent the influx of the hosts immune cells, for example, macrophages and lymphocytes, which if allowed to enter the lumen of the hollow fibers may be detrimental to the viability of the cells enclosed therein. The membrane, therefore, provides an immuno-priviledged environment that protects cells enclosed therein from an immune response. This may be an important consideration if the implanted cells are non autologous in nature.

In addition, it is contemplated that although the pores should be large enough to permit the exit of the pre-selected molecule, the pores preferably should exclude molecules, for example, antibodies and cytotoxic cytokines, having a molecular weight greater than about 150 kD. It is contemplated that exclusion of host antibodies and cytokines may enhance the longevity of the viable cells following implantation of the device into the host. As a result of the preferred pore exclusion size, it is contemplated that the hollow fibers are adapted to permit the efflux of pre-selected molecules having a molecular weight of smaller than 150 kD. Pore size is an important consideration if the cells entrapped within the capsule are not autolgous cells. Accordingly, it is appreciated that if the pre-selected molecule has a molecular weight exceeding 150 kilo daltons, for example, Factor VIII which has a molecular weight of about 330 kilo daltons, then the cells that produce and secrete the pre-selected entrapped within the hollow fiber should be autogenic in nature thereby minimizing any immune response directed against and therefore to extend the longevity of the viable cells. However, if the pre-selected molecule has a molecular weight less than 150 kilo daltons, for example, Factor IX (about 56 kilo daltons), $\alpha_1$ anti-trypsin (about 52 kilo daltons) and erythropoietin (about 36 kilo daltons), then it is anticipated that any cell type may be entrapped with the hollow fiber, although autogeneic cells are preferred.

The hollow fibers comprising, or for incorporation within, the capsule may be produced from biocompatible polymers which include, but are not limited to, polyvinylchloride, polyvinylidene fluoride, polyurethane isocyanate, polyalginate, cellulose acetate, cellulose diacetate, cellulose triacetate, cellulose nitrate, polysulfone, polystyrene, polyurethane, polyvinyl alcohol, polyacrylonitrile, polyamide, polymethylmethacrylate, polyethylene oxide, polytetrafluoroethylene or copolymers thereof. A summary of currently available hollow fibers, including methods of manufacture and the names of commercial suppliers, is set forth in Radovich (1995) "*Dialysis Membranes: Structure and Predictions*," Contrib Nephrol., Basel, Karger, 113:11–24, the disclosure of which is incorporated herein by reference. In addition, polytetrafluorethylene polymer hollow fibers are available commercially from Impra, Inc., Tempe, Ariz. or W. L. Gore and Associates, Flagstaff, Ariz.

If enough cells can be implanted in a single hollow fiber to produce a desirable level of the pre-selected molecule in the blood stream then the capsule of the invention, preferably will contain a single hollow fiber (see, for example, FIG. 1). Alternatively, if the requisite number of cells cannot be incorporated into a single hollow fiber then the appropriate number of cells may be entrapped within a bundle of hollow fibers wherein bundle of fibers are further encapsulated within a second macroporous outer membrane (see, for example, FIG. 2). The porous outer membrane preferably defines pores that do not affect the diffusion rates of nutrients and cell metabolites into, and out of the cell-containing hollow fibers. The purpose of the outer membrane is to hold the bundle of fibers together and not to limit diffusion of oxygen and nutrients into the hollow fibers or the diffusion of waste products, i.e., carbon dioxide, and the pre-selected molecule out of the hollow fibers. In such configurations, the resulting bundles of hollow fibers usually will have an external diameter sufficient to permit entrapment by the capsule of the blood permeable element. In addition, a bundle of hollow fibers may be held together by end caps (see, for example, end caps 40 in FIG. 6A). Alternatively, the hollow fibers may be encased within a biocompatible gel, for example, an autologous blood clot prepared from blood extracted from the intended recipient, thereby to produce a plug that may be captured by the blood permeable element (see, for example, plug 50, in FIG. 6C). In addition, it is contemplated, that even if the capsules are too small to be captured by the blood permeable element then they may be held in contact with the blood permeable element means of a hook or tether (see, for example, tether 60 in FIG. 6D). It is contemplated that the optimal configuration for each blood permeable element and capsule may be determined without undue experimentation by the skilled practitioner.

Viable Cells.

It is contemplated that a variety of cell types may be used in the practice of the instant invention. The cells preferably are eukaryotic cells and most preferably are mammalian in origin. Furthermore, the implanted cells most preferably are autogeneic, i.e., the implanted cells are derived from the intended recipient. However, as discussed above, because the cells of the invention may be enclosed in an immuno-priviledged environment within a semi-permeable membrane, for example, when the pre-selected molecule has a molecular weight less than 150 kilo daltons, it is contemplated that allogeneic cells, i.e., cells derived from an another individual within the same species as the intended recipient, or alternatively xenogeneic cells, i.e., cells derived from a species other than the species of the intended recipient, may be used in the practice of the invention.

The cells incorporated within the device preferably are isolated, established cells or cell lines that produce and secrete the pre-selected molecule of interest. Such cells or cell lines usually are isolated by standard cell culture and screening procedures well known and thoroughly documented in the art. Reviews discussing such conventional culture and screening procedures include, for example, "*Tissue Culture, Methods and Applications*" (1973) Kruse and Paterson, Eds., Academic Press, New York, San Francisco, London; "*Culture of Animal Cells, A Manual of Basic Technique*," Second Edition (1987) Freshney, Ed., Wiley-Liss, New York, Chichester, Brisbane, Toronto, Singapore; "*Cell Biology, A Laboratory Handbook*" (1994) Celis, Eds., Academic Press; and "*Control of Animal Cell Proliferation*" (1985) Boyton and Leffert, Eds., Academic Press., the disclosures of which are incorporated herein by reference.

Although the cells or cell lines of interest preferably are isolated from the recipient and expanded by standard cell culture methodologies prior to implantation, it is contemplated that useful cells or cell lines may be isolated from individuals of the same species other than the intended recipient. Alternatively, useful cells or cell lines may be isolated from individuals belonging to other species, i.e., of porcine, murine, equine, bovine, simian, canine or feline origin. For example, isolated fetal porcine ventral mesencephalon cells that produce and secrete dopamine have been implanted into human brain tissue to alleviate the symptoms associated with Parkinson's disease (Lindwall et al. (1990) *Science* 575–577).

To be useful, the cells should produce and secrete the pre-selected molecule of interest either constitutively or in response to ambient conditions. The practitioner by judicious choice of cells and cell lines may produce an implantable drug delivery device for the treatment of a variety of diseases. It is understood, however, that the cell type will depend upon the disease or symptom to be treated. For example, in order to produce a device suitable for the treatment of erythropoietin deficient anemia, the practitioner may incorporate erythropoietin producing cells into the device of the invention. Although any cell that produces erythropoietin may be used, it is believed that optimal cell types produce and secrete erythropoietin responsive to their environment, i.e., the level of dissolved oxygen in the blood stream. For example, cell lines that produce and secrete erythropoietin in response to variations in the level of dissolved oxygen have been isolated and characterized. See for example, U.S. Pat. No. 4,393,133 and Goldberg et al. (1987) *Proc. Natl. Acad. Sci. USA*. 84: 7972–7976, the disclosures of which are incorporated herein by reference. Accordingly, the incorporation of any cell or cell line that produces erythropoietin in response the oxygen carrying potential of the blood may be useful is in the practice of the invention.

Similarly, a device containing insulin producing cells may be used in the treatment of insulin dependent diabetes mellitus. Cells having utility in such a device, preferably are isolated from either healthy individuals of the same species as the recipient, or from healthy members from other species, i.e., mammals of porcine, bovine, equine or simian origin. Methods for isolating, screening, and culturing insulin producing Islets and dispersed Beta cells as well as insulin producing cell lines are well known and thoroughly discussed in the art. See, for example, Lacy et al. (1976) *Diabetes* 25: 585–594; Wollheim et al. (1990) *Methods in Enzymology* 192: 188–223; and Wollheim et al. (1990) *Methods in Enzymology* 192: 223–235, the disclosures of which are incorporated herein by reference.

In addition to the use of naturally occurring cells or cell lines that produce and secrete the molecule of interest, it is contemplated that cells "tailor made" by conventional recombinant DNA methodologies may be engineered to produce and secrete a desired pre-selected molecule or a combination of such molecules. The processes for manipulating, amplifying, and recombining nucleic acids encoding a pre-selected molecule of interest generally are well known in the art, are therefore, are not described in detail herein. Methods for identifying and isolating genes encoding a pre-selected molecule are also well understood, and are described in the patent and other literature.

Briefly, the production of DNAs encoding pre-selected molecules of interest is performed using known techniques involving the use of various restriction enzymes which make sequence specific cuts in DNA to produce blunt ends or cohesive ends, DNA ligases, techniques enabling enzymatic addition of sticky ends to blunt-ended DNA, construction of synthetic DNAs by assembly of short or medium length oligonucleotides, cDNA synthesis techniques, polymerase chain reaction (PCR) techniques for amplifying appropriate nucleic acid sequences from libraries, and synthetic probes for isolating genes encoding the molecule of interest. Various promoter sequences from bacteria, mammals, or insects to name a few, and other regulatory DNA sequences used in achieving expression, and various types of host cells are also known and available. Conventional transfection techniques, and equally conventional techniques for cloning and subcloning DNA are useful in the practice of this invention and known to those skilled in the art. Various types of vectors may be used such as plasmids and viruses including animal viruses and bacteriophages. The vectors may exploit various marker genes which impart to a successfully transfected cell a detectable phenotypic property that can be used to identify which of a family of clones has successfully incorporated the recombinant DNA of the vector.

One method for obtaining DNA encoding the molecule of interest may be isolated from libraries of nucleic acids, for example, by colony hybridization procedures such as those described in Sambrook et al. eds. (1989) "*Molecular Cloning*", Coldspring Harbor Laboratories Press, NY, and/or by PCR amplification methodologies, such as those disclosed in Innis et al. (1990) "*PCR Protocols, A guide to methods and applications*", Academic Press, the disclosures of which are incorporated herein by reference. The nucleic acids encoding the molecule of interest, once isolated, may be integrated into an expression vector and transfected into an appropriate host cell for protein expression. Useful prokaryotic host cells include, but are not limited to, *E. coli*, and *B. Subtilis*. Useful eukaryotic host cells include, but are not limited to, yeast cells, insect cells, myeloma cells, fibroblast 3T3 cells, monkey kidney or COS cells, chinese hamster ovary (CHO) cells, mink-lung epithelial cells, human foreskin fibroblast cells, human glioblastoma cells, and teratocarcinoma cells.

The vector additionally may include various sequences to promote correct expression of the recombinant protein, including transcriptional promoter and termination sequences, enhancer sequences, preferred ribosome binding site sequences, preferred mRNA leader sequences, preferred protein processing sequences, preferred signal sequences for protein secretion, and the like. The DNA sequence encoding the gene of interest also may be manipulated to remove potentially inhibiting sequences or to minimize unwanted secondary structure formation.

Expression of the engineered genes in eukaryotic cells requires cells and cell lines that are easy to transfect, are capable of stably maintaining foreign DNA with an unrearranged sequence, and which have the necessary cellular components for efficient transcription, translation, post-translation modification, and secretion of the protein. In addition, a suitable vector carrying the gene of interest also is necessary. DNA vector design for transfection into mammalian cells should include appropriate sequences to promote expression of the gene of interest as described herein, including appropriate transcription initiation, termination, and enhancer sequences, as well as sequences that enhance translation efficiency, such as the Kozak consensus sequence. Preferred DNA vectors also include a marker gene and means for amplifying the copy number of the gene of interest. A detailed review of the state of the art of the production of foreign proteins in mammalian cells, including useful cells, protein expression-promoting sequences, marker genes, and gene amplification methods, is disclosed in Bendig (1988) *Genetic Engineering* 7: 91–127.

The various cells, cell lines and DNA sequences that can be used for mammalian cell expression of the pre-selected molecule are well characterized in the art and are readily available. Other promoters, selectable markers, gene amplification methods and cells also may be used to express the proteins of this invention. Particular details of the transfection, and expression protocols are well documented in the art and are understood by those having ordinary skill in the art. Further details on the various technical aspects of each of the steps used in recombinant production of foreign genes in mammalian cell expression systems can be found in a number of texts and laboratory manuals in the art, such as, for example, F. M. Ausubel et al., ed., "*Current Protocols in Molecular Biology*", John Wiley & Sons, New York, (1989), the disclosure of which is incorporated by reference herein.

For example, it is contemplated that useful Factor VIII producing cells may be prepared using conventional recombinant DNA and cell culture methodologies, and used in the treatment of Hemophilia A. For example, researchers have exploited the MFG retroviral vector system to transfer of Factor VIII cDNA into murine and human cells (primary and established cell lines). The resultant cells exhibit high levels of Factor VIII production, and that the Factor VIII—secreting cells upon transfer into immune-deficient mice produce substantial levels of Factor VIII in the plasma. See, for example, Dwarki et al. (1995) *Proc. Natl. Acad. Sci. USA*. 92: 1023–1027, the disclosure of which is incorporated herein by reference. Likewise, Factor IX producing cells may be prepared and used in the treatment of Hemophilia B. Researchers have used retroviral vectors to introduce human or canine Factor IX cDNAs into cultured primary murine myoblasts, canine myoblasts and into an established murine myoblast cell line. In all cases, the resulting stably transfected cells produce biologically active Factor IX in culture and secreted detectable amounts into culture medium before and after differentiation into myotubes. See, for example, Roman et al. (1992) *Somatic Cell and Molecular Genetics* 18: 247–248, the disclosure of which is incorporated herein by reference.

In addition, $\alpha_1$-anti-trypsin producing cells may be prepared and used in the treatment of emphysema. For example, a retroviral vector has been used to insert human $\alpha_1$-anti-trypsin cDNA into the genome of mouse fibroblasts thereby to create a clonal population of mouse fibroblasts that produce and secrete human $\alpha_1$-anti-trypsin. See, for example, Garver et al. (1987) *Science* 237: 762–764, the disclosure of which is incorporated herein by reference. Similarly, hepatocytes removed from the livers of experimental animals have been modified following transfection with a retroviral vector containing $\alpha_1$-anti-trypsin DNA. The resulting hepatocytes, upon infusion into the portal circulation of the recipient produce and secrete detectable levels of $\alpha_1$-antitrypsin for up to a month. See, for example, Crystel (1992) *Am. J. Med.* 92 (Suppl 6A) 6A 445–6A 525; and Kan et al.; (1992) *Proc. Natl. Acad. Sci. USA* 89: 89–93, the disclosures of which are incorporated herein by reference.

In addition, recombinant erythropoietin secreting cell lines may be produced and used in the treatment of erythropoietin deficient anemia. For example, myoblast clones carrying a 1.34 kilo base human erythropoietin cDNA stably produce and secrete high levels of functional human erythropoietin, and upon transfer into murine models have been shown to be effective in increasing the hematocrit levels for at least twelve weeks. See, for example, Hamamori et al. (1995) *J. Clin. Invest.* 95: 1808–1813, the disclosure of which is incorporated herein by reference.

Furthermore, it is contemplated that cells capable of expressing and secreting aldolase B may be used in the treatment of hereditary fructose intolerance; glucose-6-phosphatase producing cells may be useful in the treatment of glycogen storage disease Type I; acid $\alpha$-glucosidase producing cells may be useful in the treatment of glycogen storage disease Type II; amylo-1,6-glycosidase producing cells maybe useful in the treatment of glycogen storage disease Type III; muscle phosphorylase may be useful in the treatment of glycogen storage disease Type IV; galactose-1-phosphate uridyl transferase producing cells may be useful in the treatment of galactosemia; phenylalanine hydroxylase producing cells may be useful in the treatment of phenylketonuria; tyrosine aminotransferase producing cells may be useful in the treatment of tyrosenemia; adenosine deaminase producing cells may be useful in the treatment of combined immunodeficiency disease; phorphobilinogen deaminase and URO decarboxylase producing cells may be useful in the treatment of porphyria; $\alpha$-iduronidase and induronate sulfatase producing cells may be useful in the treatment of mucopolysaccharidoses; sphingomyelinase producing cells may be useful in the treatment of Neimann-Pick disease; glucocerebrosidase producing cells may be useful in the treatment of Gauchers syndrome; $\alpha$-galactosidase producing cells may be useful in the treatment of Fabry's disease; von Willebrand Factor producing cells may be useful in the treatment of von Willebrand's disease; and antithrombin producing cells may be useful in the treatment of antithrombin deficiency. All of the aforementioned cells and cell types may be produced using conventional recombinant DNA and equally conventional cell culture methodologies. It is understood that the aforementioned examples are not meant to be limiting in any way, because, it is contemplated that any cell or cell line that produces and secretes a pre-selected molecule useful in alleviating the symptoms associated with a particular condition, once isolated, may be used in the practice of the invention.

The penultimate expression vehicles for expression of the pre-selected molecule preferably are cells of eukaryotic, most preferably mammalian origin. Eukaryotic cells may be better suited to the development of regulated cells that produce and secrete the pre-selected molecule in response to an external stimulus. It is contemplated, however, that under particular circumstances, for example, where no regulation mechanism is required and the pre-selected molecule can be produced constitutively, engineered prokaryotic cells may also be useful in the practice of the invention.

For example, under particular circumstances, for example, during the use of polysulfone hollow fibers, the formation or capture of thrombii on or around the device may affect the flow of blood around the device and/or the diffusion of nutrients or metabolites into or out of the hollow fibers. Under, these circumstances, it is contemplated that a cell type that constitutively produces and secretes an anti-coagulant, for example, tissue plasminogen activator, streptokinase, urokinase, hirudin or the like, into the blood stream also may be included within a hollow fiber. Therefore, the artisan may produce a device containing cells that either on their own or in combination produce an anticoagulant in addition to another therapeutic protein.

By way of example, it is contemplated that a gene encoding the. anti-coagulant protein huridin may be introduced into a host cell by conventional gene transfer methodologies. The local production of hirudin by endothelial cells may prove especially attractive in preventing thrombosis at vascular sites. Studies have shown that hirudin is an effective anticoagulant in vivo and is superior to heparin in experimental animal models of thrombosis following arterial injury (Haskel et al. (1991) *Circulation* 83: 1048–1056; Heras et al. (1990) *Circulation* 82: 1476–1484). For example, the hirudin encoding gene may be isolated by standard PCR protocols and ligated into a retroviral expression vector, for example pMFG Moloney murine leukemia tumor virus (Dranoff et al. (1993) *Proc. Natl. Acad. Sci. USA* 90: 3539–3542) downstream of a nucleic acid sequence encoding a signal sequence for vonWillebrand factor (vWF). The vector subsequently may be packaged into $\phi$-crip, an amphotropic, replication defective recombinant retrovirus (Danos et al. (1988) *Proc Natl. Acad. Sci. USA* 85: 6460–6464). Endothelial cells, i.e., rabbit endothelial cells or human umbilical vein endothelial cells, subsequently may be infected with the recombinant retrovirus, which results in the transfer of the hirudin gene into the genome of the endothelial cell. The transfected endothelial cells subsequently constitutively produce and secrete the recombinant hirudin gene product.

Preparation of the Capsule

Once appropriate cells or cell lines that produce and secrete the pre-selected molecule have been isolated or produced, the cells or cell lines thereafter are cultured in the hollow fibers which are used to produce the capsule. The preferred method for introducing the cells into, as well as culturing the cells within the hollow fibers is by means of a commercial bioreactor. A list of manufacturers of commercially available bioreactors is set forth in "*Genetic Engineering News*", Feb. 1, 1995, the disclosure of which is incorporated by reference. Preferred bioreactors useful in the practice of the invention include: Tricentric™ and Mab-Max™ bioreactors from Setec, Livermore, Calif.; Cell-Pharm™ Micro Mouse™ from Unisyn Technologies, Milford, Mass.; Cellmax™ Quad from Cellco, Inc., Germantown, Md.; and Vitafiber II Hollow Fiber Cell Culture System from Amicon, Inc., W.R. Grace and Co., Beverly, Mass.

Typically, a suspension of cells that produce and secrete the pre-selected molecule in cell culture medium is seeded into a bioreactor by infusing cell containing medium into the hollow fibers of the bioreactor. This step results in the capture of the cells within the hollow fibers. Thereafter, the cells are cultured under the optimal culture conditions for the particular cell type in accordance with the manufacturers instructions.

The resulting hollow fibers subsequently may be implanted either alone or as a bundle of hollow fibers in combination with the blood permeable element into the vasculature of the recipient. Methods for implantation are discussed below.

Implantation of the Device

The device of the invention preferably is inserted into the vasculature of the host by a non-surgical or minimally invasive surgical procedure. More specifically, it is contemplated that the devices of the invention may be introduced by a variety of catheter-based devices that have been developed for implanting blood clot anti-migration filters into the vasculature.

For example, U.S. Pat. Nos. 5,147,379 and 3,952,747, and International Patent Application No. PCT/US92/08366, the disclosures of which are incorporated herein by reference, describe catheter-based devices and methods for implanting blood clot anti-migration filters into the vasculature of a recipient. Typically, the catheter-based filter insertion instruments comprise: a carrier for supporting a blood clot anti-migration filter in a collapsed, compact state; an ejector mechanism, usually located within the carrier for ejecting the filter at the pre-selected site; and an elongated, flexible tube connected to the carrier for advancing the carrier along the blood vessel to the pre-selected location. Once introduced to the preferred location in the blood vessel, the filter is ejected from the carrier. When self opening and implanting filters are used, the filter is simply ejected from the carrier, whereupon the filter anchors itself to the wall of the blood vessel. If, however, a filter to be manually opened and anchored is used, then the insertion instrument may contain additional means for effecting such opening and anchorage steps. It is contemplated, however, that the skilled practitioner may insert the commercially available blood clot anti-migration filter using filter insertion instruments and methods as recommended by the manufacturer of the filter.

For example, in a preferred embodiment, the device of the invention comprises a filter element, such as the ones described in U.S. Pat. Nos. 4,817,600 and 5,059,205, that are known as Greenfield® vena cava filters and available commercially from Medi-tech®, Boston Scientific Corp., Watertown, Mass. The Greenfield filters are purchased pre-loaded into a introducer catheter. Accordingly, it is contemplated that a physician may implant a filter element, such as the ones described in U.S. Pat. Nos. 4,817,600 and 5,059, 205 in accordance with the Medi-tech®'s "instructions For Use" that are provided with the filters. Accordingly, Medi-tech®'s "Instructions for Use" are incorporated herein by reference, and described below.

Briefly, the filters, typically are inserted through the internal jugular or femoral vein by percutaneous puncture. During percutaneous insertion, and after a conventional cavogram, either the jugular or the femoral vein is punctured with a needle and a guide wire inserted into the vessel through the needle. Then, a combined sheath/dilator unit is pushed into the vein over the guide wire until the end of the sheath is located beyond the implant site. While holding the sheath in place, the dilator and guidewire are removed, leaving the sheath behind. The sheath acts as an access to permit the insertion of the introducer catheter, which contains a carrier holding the filter. The sheath is flushed with sterile heparinized saline to prevent potential thrombus formation within the sheath which may occur during insertion of the introducer catheter. The introducer catheter is advanced into, but not beyond the end of, the sheath until the tip of the filter carrier capsule is positioned adjacent to the implant site. Then, the sheath is retracted onto the introducer catheter until the carrier capsule is completely exposed. Then, the filter is pushed out of the carrier capsule by a pusher mechanism, whereupon the legs of the filter spring outward and engage the inner wall of the blood vessel thereby anchoring the filter in position. Once the filter has been ejected and anchored in the blood vessel, a capsule or capsules containing the viable cells likewise may be introduced via the same catheter into the blood vessel at a position upstream of the anchored filter. Then, the introducer catheter is removed from the vessel through the sheath. Once the introducer catheter has been removed, the sheath is also removed, and the puncture site compressed until homeostasis is achieved.

It is understood that the preferred location for implantation of the device within the systemic circulation, however, may depend upon the intended use of the device. For example, in some situations it is contemplated that it may be desirable to introduce the devices via the femoral or jugular veins and then anchor the blood permeable element at a location within a natural vein, such as, an inferior vena cava, a superior vena cava, a portal vein or a renal vein. Alternatively, the device of the invention may be anchored in a synthetic vein, such as a vein developed from a surgically-developed arteriovenous fistula. If, however, the device is to be used in hormone replacement therapy the physician may choose to implant the devices at a location downstream of the natural site of production of the preselected molecule. For example, $\alpha_1$-anti-trypsin typically is produced by liver hepatocytes; accordingly, it may be desirable to introduce and anchor an $\alpha_1$-antitrypsin producing device of the invention downstream of the liver, for example, in the hepatic vein. In addition, as mentioned above, insulin is produced by Beta cells of the pancreas; accordingly it may be desirable to anchor an insulin producing device of the invention within the portal vein downstream of the pancreas.

It is understood, however, that the physicians judgment based upon clinical circumstances should determine on a case by case basis the optimal mode for introducing the device as well as the optimal location for anchoring the device. Such judgments are contemplated to be within the scope of expertise of the skilled physician.

Practice of the invention will be still more fully understood from the following examples, which are presented herein for illustration only and should not be construed as limiting the invention in any way.

EXAMPLE 1

Growth of Erythropoietin Producing Cells in Culture

Erythropoietin is a hormone that is produced in specialized cells in the kidney and released into the circulation when the oxygen delivery to these specialized cells declines. Under hypoxic conditions resulting from a decline in red blood cell mass, a decline in oxygen delivery to tissues occurs. Subsequently, the decline in dissolved oxygen content induces the specialized kidney cells to increase erythropoietin production thereby stimulating increased production of red blood cells. Upon return to normal oxygen delivery with normoxia or increased red cell mass, the enhanced production of erythropoietin is suppressed, closing the classic feedback loop. Erythropoietin although being essential for homeostasis of blood cell mass is deficient in many chronic diseases, including, for example, chronic renal failure, rheumatoid arthritis, autoimmune diseases, chronic infections, human acquired immunodeficiency syndrome and cancer.

Erythropoietin is a 36 kD glycoprotein that comprises a polypeptide chain 165 amino acids in length (Miyake et al. (1977) *J. Biol. Chem.* 252: 5558–5564). The gene for erythropoietin has been cloned, transfected into Chinese hamster ovary cells, and expressed to produce active erythropoietin (Lin et al. (1985) *Proc. Natl. Acad. Sci. USA* 82: 7580–7585). Researchers have isolated a human hepatoma derived cell line, called Hep G2, which subsequently was found to produce and secrete erythropoietin in response to varying oxygen tensions in the culture media (Goldberg et al. (1987) *Proc. Natl. Acad. Sci. USA* 84: 7972–7976). The Hep G2 cell line is described in U.S. Pat. No. 4,393,133, incorporated above, and is available through the American Type Culture Collection (ATCC), Rockville, Md. under the accession number ATCC HB 8065.

In order to demonstrate oxygen deficiency erythropoietin production Hep G2 cells were seeded into cell culture dishes and grown in a RPMI 1640 medium supplemented with 10% fetal calf serum in a humidified atmosphere of 5% $CO_2$ at a temperature of 37° C. After 3–5 days in culture, the level of dissolved oxygen in the medium was adjusted by altering the oxygen content of the oxygen supply. Under basal, well oxygenated conditions, the composition of the air supply contained approximately 21% oxygen, 5% carbon dioxide, and 74% nitrogen. Under hypoxic conditions, the composition of the air supply contained approximately 1–2% oxygen, 5% carbon dioxide, and 93–94% nitrogen.

After incubation for three days, the production of erythropoietin was measured under both well oxygenated and hypoxic conditions using a Quantikine™ IVD™ erythropoietin immunoassay kit from R & D Systems (Minneapolis, Minn.). The assays were performed in accordance with the manufacturers instructions.

Under basal well oxygenated conditions, the Hep G2 cells produced about 20 mU erythropoietin/$10^6$ cells over a time period of 24 hours. Under hypoxic conditions, the level of erythropoietin production increased to about 100–200 mU/$10^6$ cells over the same time period.

EXAMPLE 2

Growth of Erythropoietin Producing Cells in Hollow Fibers

Patients suffering from erythropoietin deficient anemia, for example, in patients suffering from end stage renal disease, require approximately 10,000 units of recombinant human erythropoietin per week ("Proceedings from ESRD Patient Management: Strategieis for Meeting the Clinical and Economic Challenges", Nissenson, ed.(1993) in *Am. J. Kid. Diseases* 22(1) Suppl). Accordingly, the average patient may be estimated to require approximately 1,000 units of erythropoietin per day. Furthermore, assuming that under stimulated conditions, Hep G2 produce greater than 200 mU/$10^6$ cells over a 24 hour period, it may be estimated that approximately $10^9$ cells may produce sufficient erythropoietin to maintain appropriate hematocrit level in such patients.

As the cells of the invention are provided in hollow fibers, it is an object of this experiment to demonstrate that erythropoietin producing cells may be grown within a hollow fiber without compromising cell viability and/or erythropoietin production.

Erythropoietin producing Hep G2 cells (approximately $4.5 \times 10^7$/ml) were seeded into hollow fibers, specifically polysulfone hollow fibers (W.R. Grace and Associates) and cellulose acetete hollow fibers (Cellco, Inc.), having a molecular weight cut-off of 50 kilo daltons and internal diameters of 210, 350 or 510 $\mu$m. The hollow fibers were previously lined with laminin or collagen Type IV. The membranes used in these experiments had pore sizes that permitted solutes having molecular weights lower than 50 kD to pass out of the hollow fiber and into the culture medium. The pore size, therefore, permitted erythropoietin (36 kilo daltons) to diffuse out of the hollow fiber and into the surrounding medium while, at the same time, preventing migration of the Hep G2 cells out of the hollow fiber. After seeding, the hollow fibers were placed in RPMI 1640 culture medium supplemented with 10% fetal calf serum and the cells grown under well oxygenated conditions (21% oxygen) at 37° C. for 2–3 weeks.

After 2–3 weeks in culture, the amount of erythropoietin secreted into the medium was assayed as described in Example 1. In addition, the hollow fibers were removed from the culture medium and fixed for histological examination to assess the presence of cell necrosis in the hollow fiber as well as the distribution of cellular messenger RNA (mRNA) encoding the recombinant erythropoietin within each micro-environment of the hollow fiber. The histology of the cells was analyzed using standard histological techniques and the cellular erythropoietin mRNA levels were assessed using a standard in situ hybridization protocol ("*In Situ Hybridization Histochemistry*" (1990) Chesselet, ed., CRC Press, Boca Raton, Ann Arbor, Boston).

The Hep G2 cells grown within the hollow fibers having internal diameters of 210 $\mu$m remained viable because the critical distance for oxygen diffusion was small enough to permit the cells to derive sufficient oxygen and nutrients from the medium. It was found, however, that Hep G2 cells grown in fibers having diameters of 350 $\mu$m exhibited necrosis at the center of the hollow fibers. Accordingly, it appears that the cells in the middle of the hollow tube became too dense to obtain sufficient nutrients and oxygen from the surrounding culture medium. The Hep G2 cells grown in fibers of internal diameters of 510 $\mu$m did not suffer from necrosis but the cell layer attached to the inner wall of the hollow fiber was about 150 $\mu$m thick. It appears that this distance correlates with the distance over which sufficient nutrients and oxygen may diffuse to maintain viability of the Hep G2 cells. Accordingly, it appears that hollow fibers having internal diameters of 510 $\mu$m may be useful in the development of devices containing Hep G2 cells because the cells may proliferate until oxygen and nutrient levels become limiting.

EXAMPLE 3

Oxygen Regulation of Erythropoietin Production of Hep G2 Cells In Hollow Fibers

The aim of this experiment is to demonstrate that erythropoietin gene expression and protein production can be regulated by the oxygen tension of the medium surrounding the hollow fibers. This experiment may be performed using either single hollow fibers or bundles of hollow fibers to measure how the rate of erythropoietin production varies with respect to the concentration of oxygen dissolved in the culture medium.

Single hollow fibers and bundled hollow fibers of varying diameters, for example, 210 $\mu$m or 510 $\mu$m collagen treated polysulfone hollow fibers (Fresenius, USA, Wallnut Creek, Calif.) having a molecular weight cut-off about 50 kilo daltons) will be seeded with Hep G2 cells and allowed to grow under optimal conditions as determined in Example 2. After maximal cell growth has been attained, the oxygen concentration of the surrounding growth medium is adjusted by altering the oxygen content of the air supply. The compositions of the air supply are modified to oxygen concentrations of 21%; 5%; 3%; 2%; or 1% oxygen. After 24 hours, the amount of human erythropoietin secreted into the medium is measured using the procedure described in Example 1.

The cells in each hollow fiber are examined for cell viability to determine whether cell viability can be maintained under low oxygen conditions within the surrounding medium. Furthermore, the core of cells within the hollow fiber are fixed and the erythropoietin mRNA levels throughout the core determined by the standard in situ hybridization procedure used in Example 2.

It is anticipated that using this type of experiment, the viability of the cells and the production of erythropoietin may be measured to determine how many cells may be introduced into a hollow fiber and how many hollow fibers must be used in a device of the invention to produce the desired amount of erythropoietin. Both single and bundled hollow fiber constructs may be tested to determine whether scale up affects the oxygen dependent erythropoietin production of the cells.

EXAMPLE 4

Implantation of Erythropoietin Producing Cells In Vivo

The aim of this experiment is to determine the viability of Hep G2 cells following implantation of hollow fibers containing Hep G2 into the systemic circulation of an animal.

Experimental dogs are anesthetized with ketamine. While anesthetized, and by means of fluoroscopic guidance, a titanium Greenfield® vena cava filter, such as the one described in U.S. Pat. No. 5,059,205, is introduced by means of a catheter into a femoral vein. When the filter is positioned correctly within the inferior vena cava, as determined by fluoroscopy, the filter is ejected from the insertion device. Once discharged, the filter's leg hooks instantly secure the filter to the vena cava wall.

Then, Hep G2 containing hollow fibers prepared in accordance with the optimal conditions found in Example 3 are prepared for intravenous implantation upstream of the anchored Greenfield vena cava filter. The hollow fibers are prepared for injection by encasing them within a fibrin blood clot produced from blood removed from the host animal. In addition, conventional radioopaque platinum tags are incorporated into the hollow fibers to ensure appropriate placement of the fibers and to assist in retrieval of the fibers after the sacrifice of the animal. Then, the fibrin clot containing the hollow fibers is administered through the intravenous catheter upstream of the anchored Greenfield® vena cava filter. The fibrin clot containing the hollow fibers is captured and retained in place within the inferior vena cava by the filter.

Then, the filter insertion device is removed from the animal and the animal allowed to recover from anesthesia.

The animals subsequently are observed at varying time intervals after implantation. After a postoperative period ranging from about 2 weeks to about 6 months the animals are sacrificed and the hollow fibers retrieved for cell viability analysis. In addition the levels of erythropoietin mRNA in various micro-environments within the hollow fiber are determined by in situ hybridization using the method described in Example 1.

It is anticipated that the implanted cells within the capsule remain viable and that there are detectable levels of cellular erythropoietin mRNA production within the implanted cells.

EXAMPLE 5

Implantation of Erythropoietin Producing Cells into Animals Suffering From Erythropoietin Deficient Anemia The aim of this experiment is to determine whether a device of the invention comprising viable Hep G2 cells, following implantation into a mammal, may ameliorate the symptoms associated with erythropoietin deficient anemia.

Experimental dogs (1 and ⅔ nephrectomized dogs) are anesthetized with ketamine. While anesthetized, and by means of fluoroscopic guidance, a titanium Greenfield® vena cava filter, is inserted by means of a catheter via a femoral vein into the inferior vena cava. When the filter is positioned correctly within the inferior vena cava, as determined by fluoroscopy, the filter is ejected from the insertion device and anchored to the wall of the inferior vena cava.

Then, the Hep G2 containing hollow fibers prepared in accordance with the optimal conditions found in Example 4 are prepared for intravenous implantation upstream of the anchored Greenfield® vena cava filter. The hollow fibers are prepared for injection by encasing them within a fibrin blood clot produced from blood removed from the host animal. In addition, conventional radioopaque platinum tags are incorporated into the hollow fibers to ensure appropriate placement of the fibers and to assist in retrieval of the fibers after the sacrifice of the animal. Then, the fibrin clot containing the hollow fibers is administered through the intravenous catheter upstream of the anchored Greenfield® vena cava filter. The fibrin clot containing the hollow fibers is captured and retained in place within the inferior vena cava by the filter.

The filter insertion device is removed from the animal and the animal allowed to recover from anesthesia. Thereafter, the hemocrit and erythropoietin levels are measured at varying time intervals after implantation. After a postoperative period ranging from about 2 weeks to 6 about months the animals are sacrificed and the hollow fibers retrieved for cell viability analysis. In addition the levels of erythropoietin mRNA in various microenvironments within the hollow fiber are determined by in situ hybridization using the method described in Example 1. Control experiments wherein a non cell containing device is implanted into a nephrectomized dog and wherein a cell containing device is implanted into a normal dog also will be performed.

It is anticipated that nephrectomized dogs implanted with an erythropoietin producing device of the invention will exhibit elevated erythropoietin and hematocrit levels and maintenance of homeostatis relative to nephrectomized dogs treated with a non cell containing device. In addition, it is contemplated that cellular erythropoietin mRNA levels will be higher in cells implanted into nephrectomized dogs than non-nephrectomized dogs.

EXAMPLE 6

Isolation and Culture of Insulin Producing Cells in Culture

Insulin is a 5.8 kilo dalton peptide hormone comprising two polypeptide chains connected by disulfide bonds. Insulin is produced by specialized cells (Beta cells of the Islets of Langerhans) located in the pancreas in response to circulating levels of glucose in the blood stream. In response to elevated levels of glucose, insulin is produced thereby stimulating glycogen synthesis in the liver and muscles. The inability of a mammal to produce insulin in an amount sufficient to maintain euglycemia results in the condition of diabetes mellitus, which to date has been controlled by parenteral administration of exogenously produced insulin.

Methods for isolating and culturing Islets and Beta cells are thoroughly documented in the art. See, for example, Lacy et al (1976) *Diabetes* 25: 484–493; Wollheim et al. (1990) *Methods in Enzymology* 192: 188–223; and Wollheim et al. (1990) *Methods in Enzymology* 192: 223–235.

For example, in a collagenase based procedure, collagen pretreated tissue pancreatic tissue is excised from the donor mammal. After collagenase treatment, Islets of Langerhans are filtered through a filter having approximately 400 $\mu$m mesh holes, and patches that pass through the filter are harvested into a tube containing Hank's-HEPESbovine serum albumin (BSA) buffer. Then, the patches are separated from other cells by density gradient centrifugation upon a Histopaque 1077 containing gradient. The Islets are harvested and transferred into a cell culture dish containing Hank's-HEPES-BSA solution. Upon resuspension, and with the aid of a dissecting microscope, the Islets are picked up by a siliconized pasteur pipette, and transferred to a centrifuge tube containing Hank's solution. The Islets are harvested by centrifugation, resuspended in RPMI 1640 tissue culture medium supplemented with antibiotics and 10% fetal calf serum and incubated at 37° C. in an atmosphere containing 5% carbon dioxide.

After incubation for five days, the level of insulin secretion into the medium is measured using a radioimmunoassay procedure "Sigma Immuno-file" provided by Sigma Chemical Co., St. Louis, Mo. for use with Sigma product number I8510. It is anticipated that the isolated Islets produce and secrete detectable levels of insulin into the cell culture medium.

EXAMPLE 7

Growth of Insulin Producing Cells in Hollow Fibers

It has been determined using Islet cells implanted into pancreatized dogs that about $2 \times 10^5$ Islet cells maintain endocrine function in a 20 kg dog. Assuming $10^4$ Islet cells per kilo, it is estimated that a 50 kg human would likely require about $10^5$ Islet cells to maintain endocrine function. Assuming that hollow fibers having an internal diameter of about 250 $\mu$m are used in the device of the invention, and further that Islet patches 200 $\mu$m in diameter area isolated, it is estimated that about 250 Islets may be inserted into a 5 cm hollow fiber. Accordingly, 1000 of such fibers would yield a device containing about $2.5 \times 10^5$ Islets.

As the cells of the invention are provided in hollow fibers, an object of this experiment is to determine whether insulin producing Islets cells can be grown within a hollow fiber without compromising cell viability and/or insulin production.

Approximately 200 Islets isolated in Example 6 are seeded into hollow fibers, specifically, polysulfone hollow fibers (W.R. Grace and Associates) and cellulose acetete hollow fibers (Cellco, Inc.), having molecular weight cut-off of 50 kilo daltons and internal diameters of 210, 350 or 510 $\mu$m. The membranes used in these experiments have pore sizes that permit solutes having molecular weights lower than 50 kD, and therefore insulin to pass therethrough while at the same time preventing migration of the Islets out of the hollow fiber. It should be noted that in order to produce Islets small enough to be introduced into the 210 μm hollow fibers, the Islets produced by collagenase treatment should be filtered through a mesh having a pore size of about 190 μm. After seeding, the hollow fibers are placed in RPMI 1640 culture medium supplemented with 10% fetal calf serum and grown at 37° C. for 2–3 weeks.

After 2–3 weeks in culture, the amount of insulin secreted into the medium is assayed as described in Example 6. In addition, the hollow fibers are removed from the culture medium and fixed for histological examination to assess cell viability within the hollow fiber as well as the distribution of cellular insulin protein levels within each micro-environment of the hollow fiber. The histology of the Islets are analyzed using standard histological methodologies and the cellular insulin protein levels assessed using a standard immunohistochemical procedures (See, for example, "Immunocytochemistry, Practical Applications in Pathology and Biology", Polak and Van Noorden, eds. (1983) Wright PSG, Bristol, London, Boston, and "Immunochemical Methods in Cell and Molecular Biology", Mayer and Walker, eds. (1983) Academic Press, London, San Diego, New York, Boston, Sydney, Tokyo, Toronto).

It is contemplated that the Islet cells encapsulated within the hollow fibers remain viable and produce detectable levels of insulin.

EXAMPLE 8

Glucose Regulation of Insulin Production by Islets in Hollow Fibers

The aim of this experiment is to demonstrate that insulin production can be regulated by the level of glucose in the medium surrounding the hollow fibers. This experiment may be performed using either single hollow fibers or bundles of hollow fibers to measure how the rate of insulin production varies with respect to the glucose level of the culture medium.

Single hollow fibers and bundled hollow fibers of varying diameters, for example, 210 μm or 510 μm (collagen treated polysulfone hollow fibers (W.R. Grace and Associates) and cellulose acetete hollow fibers (Cellco, Inc.), having molecular weight cut-off of about 20–50 kilo daltons) will be seeded with Islets and allowed to grow under optimal conditions as determined in Example 7. After seven days in culture, the culture medium is replaced with fresh culture medium supplemented with glucose ranging in concentration from about 100 to about 500 mg/dL. After 24 hours, the amount of insulin secreted into the medium is measured, using the procedure described in Example 6.

The Islets in each hollow fiber are examined for cell viability to determine whether cell viability can be maintained under conditions that simulate in vivo conditions. Furthermore, the core of cells within the hollow fiber are fixed and insulin protein levels throughout the core are determined by a standard immunohistochemical procedure, such as of the type described in Example 7

It is anticipated that using this type of experiment, the viability of the cells and the production of insulin may be measured to determine how many Islets may be introduced into a hollow fiber and how many hollow fibers must be used in a device of the invention to produce the desired amount of insulin. Both single and bundled hollow fiber constructs may be tested to determine whether scale up affects glucose dependent insulin production in the Islets.

EXAMPLE 9

Implantation of Insulin Producing Islet Cells In Vivo

The aim of this experiment is to determine the viability of Islet cells following implantation of hollow fibers containing such cells into the systemic circulation of an animal.

Experimental dogs are anesthetized with ketamine. While anesthetized, and by means of fluoroscopic guidance, a titanium Greenfield® vena cava filter, is introduced by means of a catheter into a femoral vein. When the filter is positioned correctly within the inferior vena cava, as determined by fluoroscopy, the filter is ejected from the insertion device. Once discharged, the filter's leg hooks instantly secure the filter to the vena cava wall.

Then, Islet cell containing hollow fibers prepared in accordance with the optimal conditions found in Example 8 are prepared for intravenous administration and implantation within the anchored Greenfield® vena cava filter. The hollow fibers are prepared for injection by encasing them within a fibrin blood clot produced from blood removed from the host animal. In addition, conventional radioopaque platinum tags are incorporated into the hollow fibers to ensure appropriate placement of the fibers and to assist in retrieval of the fibers after the sacrifice of the animal. Then, the fibrin clot containing the hollow fibers is administered through the intravenous catheter upstream of the anchored Greenfield® vena cava filter. The fibrin clot containing the hollow fibers is captured and retained in place within the inferior vena cava by the filter.

The filter insertion device is removed from the animal, and the animal is allowed to recover from anesthesia. Subsequently, the animals subsequently are observed at varying time intervals after implantation. After a postoperative period ranging from about 2 weeks to about 6 months, the animals are sacrificed and the hollow fibers retrieved for cell viability analysis. In addition, the levels of insulin protein production in various micro-environments within the hollow fiber are determined by an immunohistochemical procedure.

It is anticipated that the implanted Islet cells encapsuled within the capsule remain viable and that there are detectable levels of cellular insulin production within the implanted cells.

EXAMPLE 10

Implantation of Insulin Producing Cells in Animals Suffering From Insulin Deficient Diabetes The aim of this experiment is to determine whether a device of the invention comprising viable Islet cells, following implantation into a mammal, may ameliorate the symptoms associated with insulin deficient diabetes mellitus.

Experimental (pancreatectomized) dogs are anesthetized with ketamine. While anesthetized, and by means of fluoroscopic guidance, a titanium Greenfield® vena cava filter, is introduced by means of a catheter into a femoral vein by percutaneous puncture. When the filter is positioned correctly within the inferior vena cava, as determined by fluoroscopy, the filter is ejected from the insertion device and anchored to the wall of the inferior vena cava.

Then, Islet cell containing hollow fibers prepared in accordance with the optimal conditions found in Example 9 are prepared for intravenous administration and implantation within the anchored Greenfield vena cava filter. The hollow fibers are prepared for injection by encasing them within a fibrin blood clot produced from blood removed from the host animal. In addition, conventional radioopaque platinum tags are incorporated into the hollow fibers to ensure appropriate placement of the fibers and to assist in retrieval of the fibers after the sacrifice of the animal. Then, the fibrin clot containing the hollow fibers is administered through the intravenous catheter upstream of the anchored Greenfield® vena cava filter. The fibrin clot containing the hollow fibers is captured and retained in place within the inferior vena cava by the filter.

The filter insertion device is removed from the animal, and the animal is allowed to recover from anesthesia. Then, the insulin and glucose levels are measured at varying time intervals after implantation. After a postoperative period ranging from about 2 weeks to about 6 months, the animals are sacrificed and the hollow fibers retrieved for cell viability analysis. In addition the levels of insulin protein production in various micro-environments within the hollow fiber are determined by immunohistochemistry. Control pancreactomized dogs were treated in exactly the same manner except that the insulin producing cells were omitted from the device.

It is anticipated that experimental dogs implanted with the insulin producing devices exhibit maintainence of euglycemia and have appropriate plasma insulin levels. It is contemplated, however, that the control dogs implanted with devices without the insulin producing cells do not exhibit euglycemia and do not have the appropriate plasma insulin levels.

Other Embodiments

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

Other embodiments of the invention are within the following claims.

What is claimed is:

1. An implantable device for delivering a pre-selectd molecule into systemic circulation, the device comprising in combination:
   (a) a blood permeable element comprising at least one metallic filament anchorable to an inner wall of a blood vessel which when anchored to the inner wall of the vessel permits blood in the vessel to pass therethrough; and
   (b) a capsule having disposed therein viable cells which produce and secrete the pre-selected molecule, wherein the capsule, when introduced into the vessel, is retained within the vessel by the blood permeable element and the cells disposed therein produce and secrete the pre-selected molecule into blood passing the capsule.

2. The device of claim 1, wherein the blood permeable element is an embolism anti-migration filter.

3. The device of claim 1, wherein the capsule when introduced into the vessel is retained upstream of the blood permeable element.

4. The device of claim 1, wherein the capsule comprises at least one hollow fiber.

5. The device of claim 4, wherein the hollow fiber is defined by a semi-permeable membrane.

6. The device of claim 5, wherein the semi-permeable membrane defines pores of a size sufficient to permit diffusion of the pre-selected molecule therethrough but insufficient to permit diffusion of the cells therethrough.

7. The device of claim 5 or 6, wherein the pores are dimensioned to exclude an agent in the blood which is detrimental to cell viability.

8. The device of claim 7, wherein the pores are dimensioned to prevent passage of antibodies therethrough.

9. The device of claim 5, wherein the semi-permeable membrane defines pores which permit solutes less than 150 kD to pass therethrough.

10. The device of claim 5, wherein the semi-permeable membrane comprises a material selected from the group consisting of polyvinylchloride, polyvinylidene fluoride, polyurethane isocyanate, polyalginate, cellulose acetate, cellulose diacetate, cellulose triacetate, cellulose nitrate, polysulfone, polystyrene, polyurethane, polyvinyl alcohol, polyacrylonitrile, polyamide, polymethylmethacrylate, polyethylene oxide, polytetrafluorethylene, and mixtures thereof.

11. The device of claim 1, wherein the cells are eukaryotic cells.

12. The device of claim 11, wherein in the cells are mammalian cells.

13. The device of claim 1, wherein the cells are genetically engineered cells.

14. The device of claim 1, wherein the pre-selected molecule is a protein.

15. The device of claim 14, wherein the pre-selected molecule is a hormone.

16. The device of claim 15, wherein the hormone is selected from the group consisting of erythropoietin and insulin.

17. The device of claim 1, wherein the cells produce a plurality of pre-selected molecules.

18. The device of claim 1, wherein the cells produce the pre-selected molecule in response to a stimulus in the blood.

19. The device of claim 1, wherein the cells constitutively produce the pre-selected molecule.

20. The device of claim 1, wherein the blood permeable element comprises a plurality of metallic filaments anchorable to the inner wall of the vessel.

21. The device of claim 1, filter comprising a second blood permeable element anchorable to the inner wall of the vessel, wherein the second blood permeable element, when introduced into the vessel retains the capsule within the vessel.

22. An implantable device for delivering erythropoietin into mammalian circulation, the device comprising in combination:
   (a) a filter anchorable to an inner wall of a blood vessel which when anchored to the inner wall of the vessel permits blood in the vessel to pass therethrough; and
   (b) a capsule having disposed therein viable cells which produce and secrete erythropoietin wherein the capsule, when introduced into the vessel, is retained within the vessel by the filter and the cells disposed therein produce and secrete the erythropoietin into blood passing the capsule.

23. The device of claim 22, wherein the cells produce erythropoietin in response to a stimulus.

24. The device of claim 23, wherein the cells produce erythropoietin in response to reduced oxygen carrying capacity of the blood.

25. The device of claim 22, wherein the filter comprises a metallic filament anchorable to the inner wall of the blood vessel.

26. An implantable device for delivering insulin into mammalian circulation, the device comprising:
   (a) a filter anchorable to an inner wall of a blood vessel which when anchored to the inner wall of the vessel permits blood in the vessel to pass therethrough; and
   (b) a capsule having disposed therein viable cells which produce and secrete insulin, wherein the capsule, when introduced into the vessel, is retained within the vessel by the filter and the cells disposed therein produce and secrete the insulin into blood passing the capsule.

27. The device of claim 26, wherein the cells produce insulin in response to a stimulus.

28. The device of claim 27, wherein the cells produce insulin in response to the level of glucose in the blood.

29. The device of claim 26, wherein the filter comprises a metallic filament anchorable to the inner wall of the blood vessel.

30. The device of claim 22 or 26, wherein the capsule comprises at least one hollow fiber.

31. The device of claim 30, wherein the hollow fiber is defined by a semi-permeable membrane.

32. The device of claim 31, wherein the semi-permeable membrane defines pores of a size dimensioned to minimize passage therethrough of an agent in the blood detrimental to the viability of the cells.

33. The device of claim 22 or 26, wherein the cells are eukaryotic cells.

34. The device of claim 33, wherein the cells are mammalian cells.

35. The device of claim 22 or 26, wherein the capsule when introduced into the vessel is retained upstream of the filter.

36. An implantable device for delivering a pre-selected molecule into systemic circulation, the device comprising in combination:
   (a) a blood permeable element comprising a head and a plurality of legs extending therefrom anchorable to an inner wall of a blood vessel which when anchored to the inner wall of the blood vessel permits blood in the vessel to pass therethrough; and
   (b) a capsule having disposed therein viable cells which produce and secrete the pre-selected molecule, wherein the capsule, when introduced into the vessel, is retained within the vessel by the blood permeable element and the cells disposed herein produce and secrete the pre-selected molecule into blood passing the capsule.

37. The device of claim 36, wherein the blood permeable element is an embolism antimigration filter.

38. The device of claim 36, wherein the capsule comprises at least one hollow fiber.

39. The device of claim 38, wherein the hollow fiber is defined by a semi-permeable membrane.

40. The device of claim 39, wherein the semi-permeable membrane defines pores of a size sufficient to permit diffusion of the pre-selected molecule therethrough but insufficient to permit diffusion of the cells therethrough.

41. The device of claim 36, wherein the cells are eukaryotic cells.

42. The device of claim 41, wherein the cells are mammalian cells.

43. The device of claim 36, wherein the pre-selected molecule is a protein.

44. The device of claim 43, wherein the protein is a hormone.

45. The device of claim 44, wherein the pre-selected molecule is selected from the group consisting of insulin and erythropoietin.

46. The device of claim 36, wherein the blood permeable element is metallic.

47. The device of claim 36, further comprising a second blood permeable cement anchorable to the inner wall of the vessel, wherein the second blood permeable element, when introduced into the vessel retains the capsule within the vessel.

* * * * *

UNITED STATES PATENT AND TRADEMARK OFFICE
CERTIFICATE OF CORRECTION

PATENT NO.   : 5,911,704
DATED        : June 15, 1999
INVENTOR(S)  : HUMES

It is certified that error appears in the above-identified patent and that said Letters Patent is hereby corrected as shown below:

Claim 1, column 25, line 47, "pre-selectd" should be deleted and replaced with --pre-selected--.

Claim 21, column 26, line 46, " filter" should be deleted and replaced with --further--.

Claim 36, column 28, line 8, "herein" should be deleted and replaced with --therein--.

Claim 47, column 28, line 35, "cement" should be deleted and replaced with --element--.

Signed and Sealed this

Seventh Day of December, 1999

Attest:

Q. TODD DICKINSON

Attesting Officer

Acting Commissioner of Patents and Trademarks